United States Patent [19]
Sayo et al.

[11] Patent Number: 5,919,962
[45] Date of Patent: Jul. 6, 1999

[54] PROCESS FOR PREPARING RUTHENIUM-PHOSPHINE COMPLEX

[75] Inventors: Noboru Sayo, Kanagawa; Kazushi Mashima, Osaka; Kyoko Tamao; Tetsuo Ota, both of Kyoto, all of Japan

[73] Assignee: Takasago International Corporation, Tokyo, Japan

[21] Appl. No.: 08/933,973

[22] Filed: Sep. 19, 1997

[30] Foreign Application Priority Data

Sep. 20, 1996 [JP] Japan .................................. 8-269061

[51] Int. Cl.$^6$ .............................. C07F 9/02; C07F 15/00
[52] U.S. Cl. ........................... 556/23; 556/136; 502/162
[58] Field of Search ....................... 556/23, 136; 502/162

[56] References Cited

PUBLICATIONS

Kazushi Mashima, Organometallics, vol. 16, No. 6, Mar. 19, 1996, pp. 1521–1523.

Primary Examiner—Porfirio Nazario-Gonzalez
Attorney, Agent, or Firm—Sughrue, Mion, Zinn, Macpeak & Seas, PLLC

[57] ABSTRACT

Disclosed is a ruthenium-phosphine complex represented by formula (I):

$$[\{RuX(L)\}_2(\mu\text{-}X)_3]^-[R_2NH_2]^+ \quad (I)$$

wherein R is hydrogen, an alkyl group having 1 to 5 carbon atoms, a cycloalkyl group, a substituted or unsubstituted phenyl group or a substituted or unsubstituted benzyl group; X is halogen; and L is an optically active or inactive tertiary phosphine. A process for preparing the complex (I) is also disclosed, which comprises (A) reacting a ruthenium complex represented by formula: [RuX(arene)(L)]X (wherein arene is a substituted or unsubstituted phenyl group) and an ammonium salt represented by formula (III): $R_2NH\cdot HX$, or (B) reacting a ruthenium complex represented by formula: $[RuX_2(arene)]_2$, a tertiary phosphine represented by L, and an ammonium salt (III). The complex (I) useful as a catalyst for general syntheses or asymmetric syntheses can be obtained easily in good yield.

5 Claims, No Drawings

PROCESS FOR PREPARING RUTHENIUM-PHOSPHINE COMPLEX

FIELD OF THE INVENTION

This invention relates to a novel ruthenium-phosphine complex and a process for preparing the same.

FIELD OF THE INVENTION

Numerous organic synthesis reactions using a transition metal complex as a catalyst have been developed and utilized for diverse purposes. Various asymmetric catalysts particularly for asymmetric hydrogenation have been reported. Ever since the report on synthesis of an asymmetric hydrogenation product having a high optical purity by asymmetric hydrogenation using a complex made up of a rhodium atom and an optically active phosphine as a ligand, there has been a large number of reports made on asymmetric hydrogenation using a complex formed of a transition metal atom and an optically active phosphine.

For example, *J. Chem. Soc., Chem. Commun.*, p. 922 (1985) and *J. Chem. Soc. Perkin Trans. I*, p. 1571 (1987) teach a technique for preparing an optically active amino acid derivative by hydrogenating an acylaminoacrylic acid derivative using a 2,2'-bis(diphenylphosphino)-1,1'-binaphthyl-ruthenium complex (hereinafter referred to as a BINAP-Ru complex).

Metallic ruthenium is relatively cheap among transition metals so that it is expected to provide industrially advantageous catalysts. The outstanding problem associated with ruthenium catalysts lies in reaction precision and applicability. It has therefore been demanded to develop a catalyst which can be prepared with ease and at low cost and exhibits high and long-lasting activity to achieve a high asymmetric yield in an asymmetric reaction, i.e., to provide an asymmetric reaction product of high optical purity.

The conventional ruthenium complexes are not satisfactory because of their several disadvantages, such that the process for preparation is complicated; the yield and stability of the complex are insufficient; the complex is made up of a complicated mixture; or the catalytic activity or duration of action is insufficient.

SUMMARY OF THE INVENTION

The inventors of the present invention previously synthesized a novel complex comprising 2,2'-bis[di(4-methoxyphenyl)phosphino]-1,1'-binaphthyl (hereinafter referred to as MeO-BINAP) and a ruthenium atom. They obtained a single crystal of the novel complex through recrystallization and subjected the single crystal to X-ray structure analysis. Having had confirmed that the MeO-BINAP-Ru complex catalyzes asymmetric reactions, they succeeded in synthesizing another group of novel ruthenium complexes structurally analogous to the MeO-BINAP-Ru complex, which were also found to be a catalyst for asymmetric reactions.

Further, the inventors have established an advantageous process for producing these novel complexes, in which an optically inactive ligand is used to provide a catalyst useful for general syntheses, or an optically active ligand is used to provide a catalyst useful for asymmetric syntheses, and a desired complex is obtained through simple operation in good yield. The present invention has been completed based on these findings.

The present invention provides a ruthenium-phosphine complex represented by formula (I):

$$[\{RuX(L)\}_2(\mu\text{-}X)_3]^-[R_2NH_2]^+ \quad (I)$$

wherein R represents a hydrogen atom, an alkyl group having 1 to 5 carbon atoms, a cycloalkyl group, a substituted or unsubstituted phenyl group or a substituted or unsubstituted benzyl group; X represents a halogen atom; and L represents a tertiary phosphine.

The ruthenium-phosphine complex (I) is preferably the one in which R is an ethyl group, X is a chlorine atom, and L is 2,2'-bis(di-3,5-dixylylphosphino)-1,1'-binaphthyl (hereinafter referred to as DM-BINAP), 2,2'-bis(diphenylphosphino)-5,5',6,6',7,7',8,8'-octahydro-1,1'-binaphthyl (hereinafter referred to as H$_8$-BINAP), 2,2'-bis[di(4-methoxyphenyl)phosphino]-1,1'-binaphthyl (hereinafter referred to as MeO-BINAP) 2,2'-bis(diphenylphosphino)- 6,6'-dimethyl-1,1'-biphenyl (hereinafter referred to as BIPHEMP), 2,2'-bis(di-p-tolylphosphino)-6,6'-dimethyl-1,1'-biphenyl (hereinafter referred to as Tol-BIPHEMP), 2,2'-bis(diphenylphosphino)-6,6'-dimethoxy-1,1'-biphenyl (hereinafter referred to as MeO-BIPHEP) or 2,2'-bis(di-p-tolylphosphino)-6,6'-dimethoxy-1,1'-biphenyl (hereinafter referred to as p-Tol-MeO-BIPHEP).

The present invention further provides a catalyst for asymmetric hydrogenation which comprises the above-described ruthenium-phosphine complex (I).

The present invention further provides a process for preparing a ruthenium-phosphine complex represented by formula (I) which comprises reacting a ruthenium complex represented by formula (II):

$$[RuX(arene)(L)]X \quad (II)$$

wherein X and L are as defined above; and arene represents a substituted or unsubstituted phenyl group, and an ammonium salt represented by formula (III):

$$R_2NH \cdot HX \quad (III)$$

wherein R and X are as defined above.

The present invention furthermore provides a process for preparing a ruthenium-phosphine complex represented by formula (I) comprising reacting a ruthenium complex represented by formula (IV):

$$[RuX_2(arene)]_2 \quad (IV)$$

wherein X and arene are as defined above, a tertiary phosphine represented by L, and an ammonium salt represented by formula (III).

DETAILED DESCRIPTION OF THE INVENTION

The tertiary phosphine (L) in formula (I) includes those represented by the following formulae (V) to (VII).

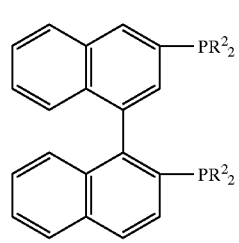

(V)

wherein R$^2$ represents a phenyl group, a 4-methylphenyl group, a 3-methylphenyl group, a 3,5-dimethylphenyl group, a 3,5-tert-butylphenyl group, a 4-chlorophenyl group, a 4-fluorophenyl group, a 4-trifluoromethylphenyl group, a 4-methoxyphenyl group, a 3,5-dimethoxyphenyl group, a 3,4-methylenedioxyphenyl group, a 3,5-dimethyl-4-methoxyphenyl group, a 2-naphthyl group, a 1-naphthyl group, a cyclohexyl group or a cyclopentyl group.

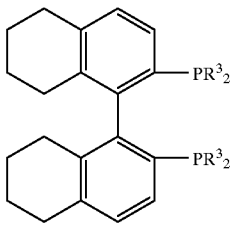

(VI)

wherein $R^3$ represents a phenyl group, a 4-methylphenyl group, a 4-methoxyphenyl group, a 3,5-dimethylphenyl group, a 3,5-dimethyl-4-methoxyphenyl group or a cyclohexyl group.

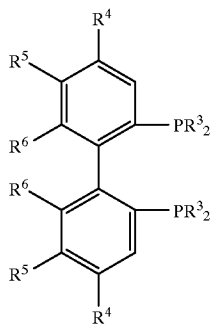

(VII)

wherein $R^3$ represents a phenyl group, a 4-methylphenyl group, a 4-methoxyphenyl group, a 3,5-dimethylphenyl group, a 3,5-dimethyl-4-methoxyphenyl group or a cyclohexyl group; $R^4$ represents a hydrogen atom, a methyl group or a methoxy group; $R^5$ represents a hydrogen atom, a methyl group, a methoxy group or a chlorine atom; and $R^6$ represents a methyl group, a methoxy group or a trifluoromethyl group.

Examples of the optically active phosphine compounds represented by formula (VII) include those described in *Chem. Pharm. Bull.*, Vol. 39, p. 1085 (1991), such as (2,2'-bis(diphenylphosphino)-4,4',6,6'-tetramethyl-5,5'-dimethoxybiphenyl represented by formula:

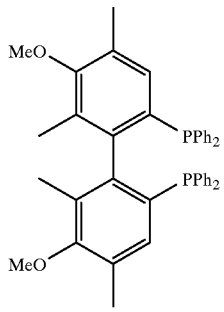

and (2,2'-bis[bis(p-methoxyphenyl)phosphino]-4,4',6,6'-tetramethyl-5,5'-dimethoxybiphenyl represented by formula:

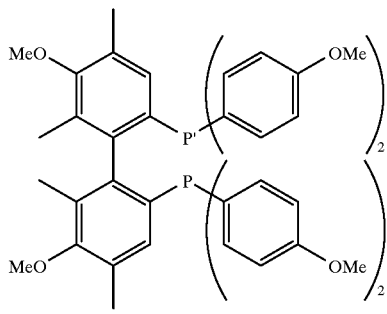

those shown in *Synlett*, p. 827 (1991), such as 2,2'-bis(siphenylphosphino)-4,4',6,6'-tetratrifluoromethylbiphenyl represented by formula:

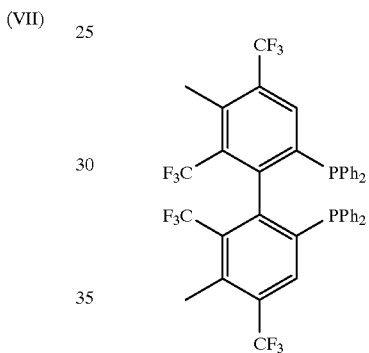

and 2,2'-bis(diphenylphosphino)-4,6-ditrifluoromethyl-4,6'-dimethyl-5'-methoxybiphenyl represented by formula:

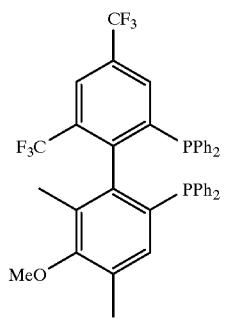

and those disclosed in *Tetrahedron:Asymmetry*, Vol. 3, p. 13 (1992), such as 2-dicyclohexylphosphino-2'-diphenylphosphino-4,4',6,6'-tetramethyl-5,5'-dimethoxybiphenyl represented by formula:

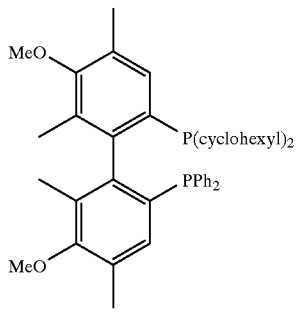

Additionally, the following optically active phosphine compounds disclosed in JP-B-4-15796 (the term "JP-B" as used herein means an "examined Japanese patent publication") are also useful.

2,2'-Diphenylphosphino-4,4',6,6'-tetramethylbiphenyl represented by formula:

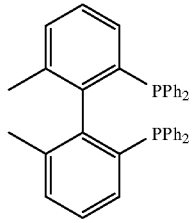

2,2'-Bis(diphenylphosphino)-4,4',6,6'-tetramethylbiphenyl represented by formula:

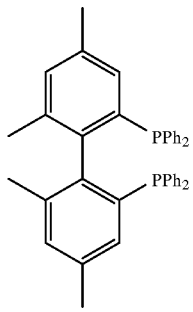

2,2'-Bis(diphenylphoshino)-3,3',6,6'-tetramethylbiphenyl represented by formula:

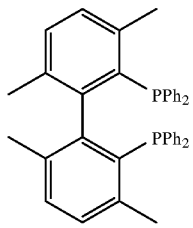

2,2'-Bis(diphenylphosphino)-4,4'-difluoro-6,6'-dimethylbiphenyl represented by formula:

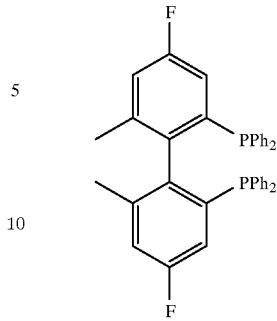

2,2'-Bis(diphenylphosphino)-4,4'-bis(dimethylamino)-6,6'-dimethylbiphenyl represented by formula:

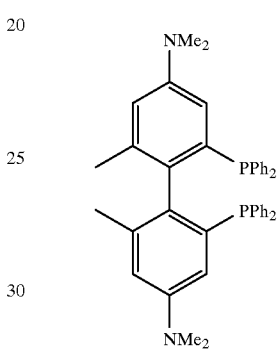

2,2'-Bis(di-p-tolylphosphino)-6,6'-dimethylbiphenyl represented by formula:

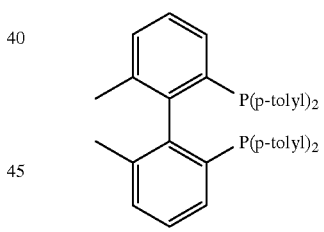

2,2'-Bis(di-o-tolylphosphino)-6,6'-dimethylbiphenyl represented by formula:

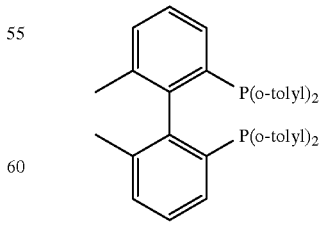

2,2'-Bis[bis(m-fluorophenyl)phosphino]-6,6'-dimethylbiphenyl represented by formula:

1,11-Bis(diphenylphosphino)-5,7-dihydrodibenzo[c.e] oxepin represented by formula:

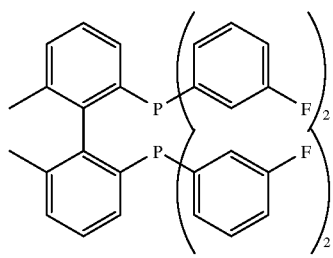

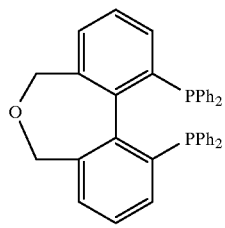

The following compounds which are disclosed in JP-A-3-5492 (the term "JP-A" as used herein means an "unexamined published Japanese patent application") are also useful.

2,2'-Bis(diphenylphosphino)-6,6'-dimethoxybiphenyl represented by formula:

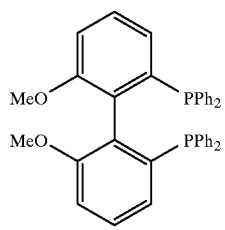

2,2'-Bis(diphenylphosphino)-5,5',6,6'-tetramethoxybiphenyl represented by formula:

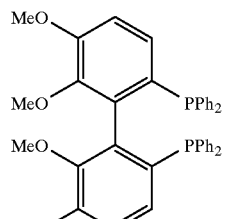

2,2'-Bis(diphenylphosphino)-4,4',5,5',6,6'-hexamethoxybiphenyl represented by formula:

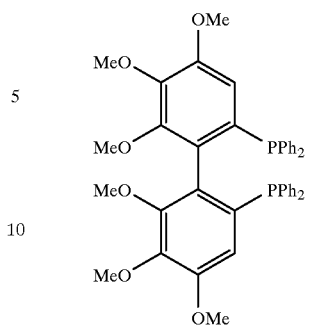

2,2'-Bis(di-p-tolylphosphino)-4,4',6,6'-dimethoxybiphenyl represented by formula:

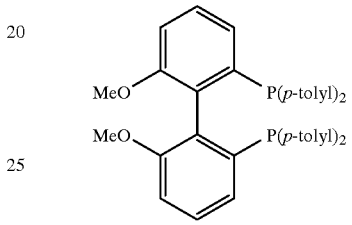

2,2'-Bis(di-p-tolylphosphino-5,5',6,6'-tetramethoxybiphenyl represented by formula:

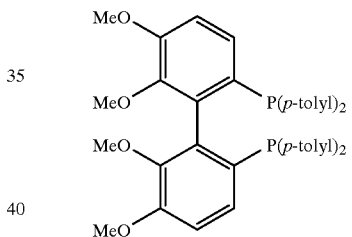

Optically active phosphine compounds further include 2,3-bis(diphenylphosphino)butane (hereafter referred to as CHIRAPHOS) represented by formula (VIII):

(VIII)

2,3-O-isopropylidene-2,3-dihydroxy-1,4-bis(diphenylphosphino)butane (hereinafter referred to as DIOP) represented by formula (IX):

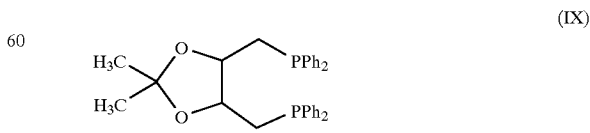

(IX)

2,4-bis(diphenylphosphino)pentane (hereinafter referred to as BDPP) represented by formula (X):

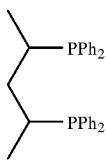

(X)

1-tert-butoxycarbonyl-4-diphenylphosphino-2-diphenylphosphinomethylpyrrolidine (hereinafter referred to as BPPM) represented by formula (XI):

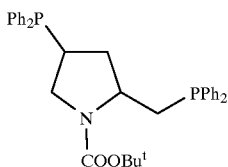

(XI)

and 1-[1',2-Bis(diphenylphosphino)ferrocenyl]ethanol (hereinafter referred to as BPPHFOH) represented by formula (XII):

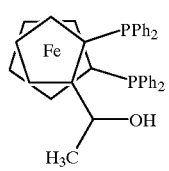

(XII)

Optically inactive tertiary phosphines include bisdiphenylphosphinoethane, bisdiphenylphosphinopropane, bisdiphenylphosphinobutane, bisdiphenylphosphinopentane, and bisdiphenylphosphinohexane.

R in formula (I) represents a hydrogen atom, a lower alkyl group, a cycloalkyl group, a substituted or unsubstituted phenyl group or a substituted or unsubstituted benzyl group. The lower alkyl group and the cycloalkyl group as R preferably include methyl, ethyl, propyl, isopropyl, butyl, isobutyl, tert-butyl and cyclohexyl groups. The substituted or unsubstituted benzyl group includes a benzyl group and a 1-phenylethyl group.

Preferred dialkylamines ($HNR_2$) include dimethylamine, diethylamine, dipropylamine, diisopropylamine, dibutylamine, diisobutylamine, di-tert-butylamine, dicyclohexylamine, dibenzylamine, 1-phenylethylamine, bis(1-phenylethyl)amine, pyrrolidine, piperidine, morpholine, and L-proline methyl ester.

X in formula (I) includes chlorine, bromine, and iodine.

Particularly preferred complexes of formula (I) are shown below:

[{RuCl(BINAP)}$_2$($\mu$-Cl)$_3$]$^-$[Et$_2$NH$_2$]$^+$
[{RuCl(Tol-BINAP)}$_2$($\mu$-Cl)$_3$]$^-$[Et$_2$NH$_2$]$^+$
[{RuCl(DM-BINAP)}$_2$($\mu$-Cl)$_3$]$^-$[Et$_2$NH$_2$]$^+$
[{RuCl(MeO-BINAP)}$_2$($\mu$-Cl)$_3$]$^-$[Et$_2$NH$_2$]$^+$
[{RuCl(H$_8$-BINAP)}$_2$($\mu$-Cl)$_3$]$^-$[Et$_2$NH$_2$]$^+$
[{RuCl(BIPHEMP)}$_2$($\mu$-Cl)$_3$]$^-$[Et$_2$NH$_2$]$^+$
[{RuCl(BICHEP)}$_2$($\mu$-Cl)$_3$]$^-$[Et$_2$NH$_2$]$^+$
[{RuCl(Tol-BIPHEP)}$_2$($\mu$-Cl)$_3$]$^-$[Et$_2$NH$_2$]$^+$
[{RuCl(MeO-BIPHEP)}$_2$($\mu$-Cl)$_3$]$^-$[Et$_2$NH$_2$]$^+$
[{RuCl(p-Tol-MeO-BIPHEP)}$_2$($\mu$-Cl)$_3$]$^-$[Et$_2$NH$_2$]$^+$
wherein "BICHEP" represents 2,2'-bis (dicyclohexylphosphino)-6,6'-dimethylbiphenyl.

"arene" in formula (II) represents a substituted or unsubstituted phenyl group. Preferred compounds from which "arene" is derived include benzene, toluene, xylene, mesitylene, p-cymene, cumene, hexamethylbenzene, ethylbenzene, methyl benzoate, ethyl benzoate, anisole, chlorobenzene, dichlorobenzene, bromobenzene, and fluorobenzene.

X in formula (II) includes chlorine, bromine, and iodine.
L in formula (II) is the same as in formula (I).
R and X in formula (III) are the same as in formula (I).
X in formula (IV) is the same as in formula (I), and "arene" in formula (IV) is the same as in formula (II).

The complexes (I) according to the present invention are synthesized through two approaches. Through one approach, the complex of the invention is obtained as a mixture with other products, which is to be purified to isolate the complex of the invention. Through another approach, which has been developed by the inventors, the complex of the invention is obtained as a single product of high purity with no need to purify the product.

A process according to the first approach for obtaining the complex (I) by purifying a mixture composed of a plurality of products comprises reacting a tertiary phosphine with a ruthenium complex represented by formula [Ru(cod)Cl$_2$]$_n$ (wherein cod represents 1,5-cyclooctadiene) in a solvent in the presence of a base (hereinafter referred to as process A).

The reaction is carried out at a temperature of 100 to 140° C., preferably 110 to 130° C., for a period of 6 to 12 hours, preferably 7 to 9 hours. The base to be used includes triethylamine. Examples of suitable solvents for the reaction include toluene and xylene. After completion of the reaction, the solvent was removed by evaporation, and the residue is recrystallized from methylene chloride and diethyl ether to obtain the complex (I) as deep red and transparent crystals.

For example, a reaction between MeO-BINAP and [Ru (cod)Cl$_2$]$_n$ in the presence of triethylamine (Et$_3$N) provides a mixture comprising [{RuCl(L)}$_2$($\mu$-Cl)$_3$]Et$_2$NH$_2$ (the complex (I) of the invention; L is MeO-BINAP), a complex having formula RuClH(L)$_2$ (L is MeO-BINAP), etc. In this particular case, the complex (I) was obtained as a main product in a yield of 37% (after recrystallization) (see Example 1 hereinafter given).

Because the starting complex [RuCl$_2$(cod)]$_n$ used in process A is a polymeric compound, there seems to be countless possible sites of cleavage, which appears to account for the formation of a plurality of products in process A. The mechanism of triethylamine's forming an ammonium salt (Et$_2$NH$_2$) is considered to resides in the release of the ethyl group from triethylamine resulting in decomposition into a proton and ethylene.

The another approach, in which the complex (I) is obtained as a pure and single product, includes the following two processes B and C.

Process B comprises reacting a ruthenium complex represented by formula (II) and an ammonium salt represented by formula (III), and process C comprises reacting a ruthenium complex represented by formula (IV), a tertiary phosphine represented by L, and an ammonium salt represented by formula (III).

The starting complexes represented by formula (II) are prepared as follows.

Of the complexes (II) those in which X is chlorine, i.e., [RuCl(arene)(L)]Cl are synthesized quantitatively by reacting [RuCl$_2$(arene)]$_2$ (prepared by a process known in the literature, e.g., G. Wikhaus, *J. Org. Chem.*, Vol. 41, p. 487 (1976) or R. A. Zelonka, *Can. J. Chem.*, Vol. 50, p. 3643 (1972)) with a tertiary phosphine L in a solvent, such as methanol, ethanol, benzene, methylene chloride or a mixture thereof, at 20 to 50° C. for 1 to 3 hours and removing the solvent by evaporation under reduced pressure.

Those in which X is bromine or iodine, i.e., [RuBr(arene)(L)]Br or [RuI(arene)(L)]I can be prepared as follows. [RuCl$_2$(arene)]$_2$ is reacted with a salt represented by formula (XII):

M$^1$Z (XII)

wherein M$^1$ represents Li, Na or K; and Z represents Br or I, in water or methylene chloride as a solvent by stirring at room temperature in the presence of a quaternary ammonium or phosphonium salt represented by formula (XIII):

R$^4$R$^5$R$^6$R$^7$QX (XIII)

wherein R$^4$, R$^5$, R$^6$, and R$^7$ each represent an alkyl group having 1 to 16 carbon atoms or a benzyl group; Q represents a nitrogen atom or a phosphorus atom; and X represents a halogen atom, as a phase transfer catalyst to obtain [RuZ$_2$(arene)]$_2$ (see Mashima et al., *J. Org. Chem.*, Vol. 59, p. 3064 (1994)).

The phase transfer catalyst (XIII) to be used include Et$_4$NCl, Et$_4$NBr, Et$_4$NI, Bu$_4$NCl, Bu$_4$NBr, Bu$_4$NI, (benzyl)Et$_3$NCl, (benzyl)Et$_3$NBr, (benzyl)Et$_3$NI, (benzyl)Pr$_3$NCl, (benzyl)Pr$_3$NBr, (benzyl)Pr$_3$NI, (C$_8$H$_{17}$)Me$_3$NCl, (C$_8$H$_{17}$)Me$_3$NBr, (C$_8$H$_{17}$)Me$_3$NI, (C$_{16}$H$_{33}$)Me$_3$NCl, C$_{16}$H$_{33}$)Me$_3$NBr, (C$_{16}$H$_{33}$)Me$_3$NI, MePh$_3$PCl, MePh$_3$PBr, MePh$_3$PI, EtPh$_3$PCl, EtPh$_3$PBr, EtPh$_3$PI, BuPh$_3$PCl, BuPh$_3$PBr, BuPh$_3$PI, (C$_8$H$_{17}$)Ph$_3$PCl, (C$_8$H$_{17}$)Ph$_3$PBr, (C$_8$H$_{17}$)Ph$_3$PI, (C$_{16}$H$_{33}$)Ph$_3$PCl, (C$_{16}$H$_{33}$)Bu$_3$PBr, and (C$_{16}$H$_{33}$)Bu$_3$PI, (C$_{16}$H$_{33}$)Bu$_3$PCl, (C$_{16}$H$_{33}$) Bu$_3$PBr, and (C$_{16}$H$_{33}$)Bu$_3$PI.

The resulting [RuZ$_2$(arene)]$_2$ and L are reacted in a solvent, such as methanol, ethanol, benzene, methylene chloride or a mixture thereof at 20 to 50° C. for 1 to 3 hours, and the solvent was removed by evaporation under reduced pressure to obtain [RuBr(arene)(L)]Br or [RuI(arene)(L)]I quantitatively.

Using the thus prepared [RuX(arene)(L)]X (II) as an intermediate, the complex of the present invention, for example, [{RuCl(BINAP)}$_2$($\mu$-Cl)$_3$]$^-$[Et$_2$NH$_2$]$^+$, can be prepared quantitatively by reacting [RuCl(benzene)(BINAP)]Cl (II) with diethylamine hydrochloride (III) (Et$_2$NH.HCl) in a solvent, such as tetrahydrofuran (THF), dioxane, dimethoxyethane (DME), dimethylacetamide (DMA), dimethylformamide (DMF) or dioxolane, at 50 to 100° C. for 5 to 20 hours and removing the solvent by evaporation.

Using [RuZ$_2$(arene)]$_2$ (IV) as an intermediate, the complex of the present invention, for example, [{RuCl(BINAP)}$_2$($\mu$-Cl)$_3$]$^-$[Et$_2$NH$_2$]$^+$, can be prepared quantitatively by reacting [RuCl$_2$(benzene)]$_2$ (IV), BINAP (L), and Et$_2$NH.HCl (III) in a solvent, such as THF, dioxane, DME, DMA, DMF or dioxolane, at 50 to 100° C. for 5 to 20 hours and removing the solvent by evaporation.

The ruthenium-phosphine complexes prepared by the above-described processes according to the present invention have been confirmed to be a pure complex as a result of analyses such as $^{31}$P-NMR.

The structure of the ruthenium-phosphine complexes according to the present invention was established as follows. The details will be shown in Example 1.

X-Ray structure analysis of the structure (I), for example, [{RuCl(MeO-BINAP)}$_2$($\mu$-Cl)$_3$]$^-$[Et$_2$NH$_2$]$^+$ represented by structural formula:

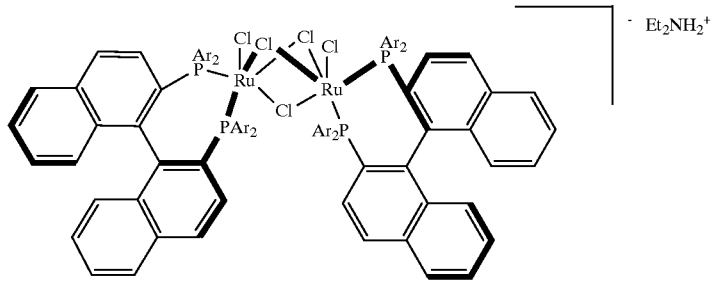

(S)-2  Ar = *p*-MeO—C$_6$H$_4$

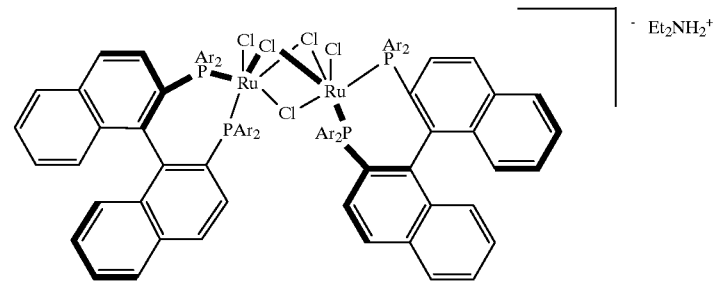

(R)-2  Ar = *p*-MeO—C$_6$H$_4$ was carried out on the single crystal sealed into a glass capillary in an argon atmosphere. The crystal was fixed on a goniometer head of a four-axis type X-ray diffractometer AFC-7R (manufactured by Rigaku K. K.), and reflection data were obtained by using MoKα as a ray source. Twenty-five strong reflections at 20° C. were selected. The crystal lattice constants of the complex were determined from 20 values of the reflections through the least-squares method. Three standard reflections were chosen from the reflection data, and observation was made for every 150 reflections. As a result, no serious intensity decay was observed during data sampling. Correction for absorption was not carried out because the linear absorption coefficient μ is small. Every reflection datum was corrected for polarization factor and Lorentz's factor. Calculations were performed using TEXSAN software, the structure image was obtained by using ORTEP software, and the crystal structure was analyzed by a direct method using SHELXS86 software.

The complexes according to the present invention are stable and exhibit high catalytic activity in asymmetric hydrogenation. That is, when the complex is used in a concentration of 1/100 to 1/10000 M based on the reaction substrate, a hydrogenation reaction proceeds rapidly to give excellent results in terms of chemical and optical purity of the hydrogenation product.

The substrates applicable to the hydrogenation reaction include allyl alcohols, such as geraniol and nerol; olefinic acids, such as α,β-unsaturated carboxylic acids, e.g., tiglic acid, dehydronaproxen, and itaconic acid; and ketones, such as methyl acetoacetate, 2-oxopropanol, and 2,4-pentanedione.

Unlike the conventional processes for preparing a ruthenium-phosphine complex which involve purification of a product comprising a mixture as obtained, the process according to the present invention requires no purification procedures and provides a desired complex as a pure and single product.

The complex obtained by the process of the invention is stable and, when used in asymmetric hydrogenation, exhibits very high activity to give excellent results in terms of chemical and optical purity of a hydrogenation product.

The present invention will now be illustrated in greater detail with reference to Examples and Application Examples, but it should be understood that the present invention is not limited thereto. Unless otherwise indicated, all the percents are by weight.

In Examples, measurements of physical properties were made with the following equipment.

$^1$H-NMR: AM400, manufactured by Bruker Inc. (400 MHz; internal standard: tetramethylsilane)

$^{31}$P-NMR: AM400, manufactured by Bruker Inc. (162 MHz; internal standard: 85% phosphoric acid)

Gas-liquid chromatography (GLC): 5890-II, manufactured by Hewlett Packard

In Application Examples, the conversion and optical purity of the product obtained were measured by GLC using the following columns.

Conversion: FFAP (25 m×0.35 mm) manufactured by GL Science.

Optical Purity: α-DEX120 (30 m×0.25 mm) manufactured by Supelco, Inc.)

EXAMPLE 1

Synthesis of [{RuCl((R)-MeO-BINAP)}$_2$(μ-Cl)$_3$]$^-$ [Et2NH$_2$]$^+$

1) Preparation of (R)-MeO-BINAP

A mixture of 1.91 g (25 mmol) of 2,2'-bis[di(4-methoxyphenyl)phosphino]-1,1'-binaphthyl, 2.5 ml (25 mmol) of trichlorosilane, 3.5 ml (25 mmol) of triethylamine, and 40 ml of xylene was stirred at 128° C. for 9 hours. To the reaction mixture was added 25% NaOH, followed by liquid-liquid separation. The aqueous layer was extracted with chloroform. The combined organic layer was concentrated, and the residue was recrystallized from toluene-ethanol to give 1.5 g (80%) of (R)-2,2'-bis[di(4-methoxyphenyl)phosphino]-1,1'-binaphthyl ((R)-MeO-BINAP) as a white solid.

Melting point: 167–169° C.

$[α]_D^{25}$: +109.2° (c=0.53, benzene)

$^1$H-NMR (CDCl$_3$) δ: 3.73 (s, 12H, OCH$_3$), 6.55–7.97 (m, 28H, aromatic)

$^{31}$P-NMR (CDCl$_3$) δ: –17.2 (s)

Mass spectrum m/e: 742 (M$^+$), 727 ((M–CH$_3$)$^+$), 635 ((M–C$_6$H$_4$OCH$_3$)$^+$), 497 (base peak, (M–P(C$_6$H$_4$OCH$_3$)$_2$)$^+$)

Elementary analysis for C$_{48}$H$_{40}$O$_4$P$_2$: Calcd. (%): C 77.62, H 5.43 Found (%): C 77.68, H 5.24

2) Preparation of MeO-BINAP-Ru Complex

A mixture of 202 mg (0.27 mmol) of the resulting (R)-MeO-BINAP, 76 mg (0.27 mol) of [RuCl$_2$(cod)]$_n$ (produced by N. E. Chemcat Ltd.), 30 ml of toluene, and 1 ml of triethylamine was heated at 110° C. for 8 hours while stirring. The reaction solution was concentrated, and the residue was recrystallized from a mixture of 3 ml of methylene chloride and 20 ml of diethyl ether to give 97 mg (37%) of [{RuCl((R)-MeO-BINAP)}$_2$(μ-Cl)$_3$]$^-$[Et$_2$NH$_2$]$^+$ as deep red crystals.

Melting point: 120° C. (with decomposition) $^1$H-NMR (CDCl$_3$) δ: 1.42 (t, 6H, J=7.4 Hz), 3.05 (m, 2H), 3.26 (m, 2H), 3.42 (s, 6H), 3.44 (s, 6H), 3.58 (s, 6H), 3.71 (s, 6H), 5.95 (dd, J=1.3 and 8.6 Hz, 4H), 6.05–6.15 (m, 8H), 6.55–6.7 (m, 6H), 6.85–6.95 (m, 2H), 7.0–7.2 (m, 6H), 7.2–7.35 (m, 4H), 7.35–7.6 (m, 20H), 7.8–7.95 (m, 2H), 7.95–8.1 (m, 4H), 8.56 (br. s, 2H) (one molecule of methylene chloride and two molecules of diethyl ether were contained).

$^{31}$P-NMR (CDCl$_3$) δ: 52.0 and 49.5 (J=38.0 Hz)

Elementary analysis for C$_{100}$H$_{92}$Cl$_5$O$_8$NP$_4$Ru$_2$(CH$_2$Cl$_2$) (OC$_4$H$_{10}$)$_2$: Calcd. (%): C, 60.26; H, 5.20; N, 0.64 Found (%): C, 60.78; H, 4.97; N, 0.62

The crystal was sealed into a glass capillary containing argon gas and subjected to X-ray structure analysis by using MoKα as a radiation. The measurement data and data concerning the analytical results are shown below. Of the reflection data, only those having an intensity higher than 3.0σ were used in performing the analysis. The crystal structure was analyzed by a direct method using SHELXS86 software, and calculations were made so that the values defined by the following formulae may be the least by least-squares method of full-matrix.

$$R = \Sigma ||Fo|-|Fc||/\Sigma |Fo| \text{ and}$$

$$R_\omega = [\Sigma \omega (|Fo|-|Fc|)^2/\Sigma \omega (|Fo|)^2]^{1/2}$$

In the above formulae, |FO| and |Fc| are the observed value and the calculated value of the structure factor, respectively, and weight w is defined by formula: $ω^{-1} = σ^2$ (Fo) = $σ^2$(Fo$^2$)/(4Fo$^2$). The coordinates of all the atoms other than hydrogen were decided by difference Fourier synthesis and calculated as anisotropic thermal vibrations. The hydrogen atoms bonded to the aromatic ring were included in the calculations, being fixed at an ideal distance (C–H=0.95 Å). These calculations were performed by using TEXSAN software.

Measurement Data and Data Concerning Analytical Results

Molecular formula: C$_{109}$H$_{114}$Cl$_7$O$_{10}$NP$_4$Ru$_2$

Formula weight: 2172.31
Crystal system: orthorhombic
Space group: C2221
a: 21.464 Å (4)
b: 22.770 Å (4)
c: 25.656 Å (4)
Z (number of molecules per unit cell): 4
V (volume of unit cell): 12538 (3) Å$^3$
Dcalcd. (calculated density): 1.151 g/cm$^3$
F(000) (number of electrons per unit cell): 4488
Radiation: MoKα
Crystal size: 0.6×0.3×0.2 mm
Linear absorption coefficient: 4.89 cm$^{-1}$
Scan mode: ω–2θ
Temperature: 20° C.
Scan speed: 16°/min
Scan width: 0.89°+0.35 tanθ
2 θmax: 55.30
Unique data (observed): 7789
Unique data (I>3σ(I)): 5444
No. of variables: 555
R (RT value or R factor): 0.062
Rω: 0.062
ΔeÅ$^{-3}$: 0.74, −1.47

| \multicolumn{5}{c}{xyz Coordinates:} |
| atom | x | y | z | B$_{eq}$ |
| --- | --- | --- | --- | --- |
| Ru(1) | 0.9473 (4) | 0.0699 (3) | 0.01912 (3) | 2.66 (2) |
| Cl(1) | 1.0302 (2) | 0.0000 | 0.0000 | 3.03 (8) |
| Cl(2) | 0.8468 (1) | 0.1158 (1) | 0.0327 (1) | 3.73 (7) |
| Cl(3) | 0.9036 (1) | −0.0202 (1) | 0.0605 (1) | 3.27 (6) |
| Cl(4) | 0.5156 (7) | 0.0691 (6) | 0.0499 (5) | 46.4 (7) |
| P(1) | 0.9894 (1) | 0.1041 (1) | 0.0945 (1) | 3.01 (7) |
| P(2) | 0.9767 (1) | 0.1518 (1) | −0.0249 (1) | 3.13 (7) |
| C(1) | 1.1110 (5) | −0.0546 (4) | 0.2489 (4) | 6.9 (3) |
| O(2) | 0.8175 (8) | 0.2019 (7) | 0.2573 (5) | 12.3 (5) |
| O(3) | 1.2367 (4) | 0.2014 (5) | −0.0982 (4) | 6.8 (3) |
| O(4) | 0.8399 (6) | 0.1984 (5) | −0.2255 (4) | 8.1 (4) |
| O(5) | 0.722 (2) | 0.052 (2) | 0.702 (2) | 37 (1) |
| N(1) | 0.7723 (8) | 0.0000 | 0.0000 | 7.3 (5) |
| C(1) | 1.0529 (6) | 0.2088 (6) | 0.0666 (4) | 3.8 (3) |
| C(2) | 1.0562 (6) | 0.1524 (5) | 0.0843 (4) | 3.4 (3) |
| C(3) | 1.1166 (6) | 0.1294 (6) | 0.0893 (5) | 4.6 (4) |
| C(4) | 1.1693 (6) | 0.1586 (7) | 0.0786 (6) | 5.3 (4) |
| C(5) | 1.1666 (7) | 0.2146 (8) | 0.0624 (6) | 5.7 (4) |
| C(6) | 1.2209 (7) | 0.2509 (10) | 0.9496 (7) | 8.1 (6) |
| C(7) | 1.2161 (9) | 0.3055 (9) | 0.0298 (8) | 8.4 (6) |
| C(8) | 1.1561 (9) | 0.3323 (7) | 0.0223 (8) | 8.5 (5) |
| C(9) | 1.1932 (7) | 9.3030 (6) | 0.0357 (6) | 6.7 (5) |
| C(10) | 1.1076 (7) | 0.2443 (7) | 0.0557 (5) | 4.7 (4) |
| C(11) | 0.9917 (6) | 0.2389 (5) | 0.0546 (5) | 3.9 (3) |
| C(12) | 0.9570 (5) | 0.2190 (5) | 0.0133 (5) | 3.7 (3) |
| C(13) | 0.8992 (5) | 0.2510 (6) | 0.0008 (5) | 4.8 (3) |
| C(14) | 0.8787 (6) | 0.2976 (6) | 0.0315 (6) | 5.7 (4) |
| C(15) | 0.9113 (6) | 0.3158 (6) | 0.0747 (6) | 6.4 (5) |
| C(16) | 0.8888 (9) | 0.3615 (8) | 0.1041 (7) | 9.5 (6) |
| C(17) | 0.919 (1) | 0.3824 (8) | 0.1442 (9) | 10.4 (7) |
| C(18) | 0.981 (1) | 0.3558 (7) | 0.1570 (7) | 9.3 (6) |
| C(19) | 1.0048 (7) | 0.3107 (3) | 0.1287 (6) | 6.6 (4) |
| C(20) | 0.9696 (6) | 0.2889 (5) | 0.0848 (5) | 4.9 (4) |
| C(21) | 1.0253 (5) | 0.0531 (5) | 0.1407 (4) | 3.4 (3) |
| C(22) | 1.0471 (7) | 0.0733 (6) | 0.1881 (4) | 5.1 (3) |
| C(23) | 1.0763 (7) | 0.055 (7) | 0.2246 (5) | 5.3 (4) |
| C(24) | 1.0854 (7) | −0.0191 (6) | 0.2164 (5) | 4.7 (4) |
| C(25) | 1.0656 (7) | −0.0403 (5) | 0.1707 (5) | 5.7 (4) |
| C(26) | 1.0350 (6) | −0.0061 (6) | 0.1326 (5) | 4.7 (3) |
| C(27) | 1.1302 (7) | −0.0292 (6) | 0.2995 (5) | 7.1 (5) |

-continued

| \multicolumn{5}{c}{xyz Coordinates:} |
| atom | x | y | z | B$_{eq}$ |
| --- | --- | --- | --- | --- |
| C(31) | 0.9384 (6) | 0.1406 (5) | 0.1398 (4) | 3.6 (3) |
| C(32) | 0.9548 (7) | 0.1849 (5) | 0.1708 (5) | 4.5 (3) |
| C(33) | 0.9172 (9) | 0.2093 (8) | 0.2106 (7) | 7.4 (6) |
| C(34) | 0.860 (1) | 0.1857 (8) | 0.2206 (7) | 6.6 (6) |
| C(35) | 0.8421 (7) | 0.1410 (8) | 0.1876 (7) | 6.8 (5) |
| C(36) | 0.8799 (6) | 0.1158 (7) | 0.1487 (4) | 5.1 (4) |
| C(37) | 0.831 (2) | 0.243 (1) | 0.2878 (9) | 21 (1) |
| C(41) | 1.0571 (6) | 0.1679 (5) | −0.0446 (4) | 3.3 (3) |
| C(42) | 1.0741 (6) | 0.2243 (6) | −0.0624 (5) | 4.6 (4) |
| C(43) | 1 1345 (7) | 0.2359 (6) | −0.0799 (5) | 5.1 (4) |
| C(44) | 1.1786 (6) | 0.1920 (7) | −0.0805 (5) | 4.4 (4) |
| C(45) | 1.1615 (5) | 0.1377 (6) | −0.0629 (6) | 5.5 (4) |
| C(46) | 1.1020 (6) | 0.1265 (5) | −0.0455 (5) | 3.8 (3) |
| C(47) | 1.2584 (7) | 0.2558 (7) | −0.1171 (6) | 6.7 (5) |
| C(51) | 0.9365 (5) | 0.1620 (5) | −0.0873 (4) | 3.2 (3) |
| C(52) | 0.8714 (6) | 0.1601 (5) | −0.0919 (5) | 3.6 (3) |
| C(53) | 0.8410 (6) | 0.1726 (6) | −0.1366 (5) | 4.5 (4) |
| C(54) | 0.8708 (7) | 0.1869 (7) | −0.1808 (6) | 5.3 (4) |
| C(55) | 0.9331 (8) | 0.1870 (6) | −0.1795 (5) | 5.9 (4) |
| C(56) | 0.9669 (6) | 0.1747 (6) | −0.1336 (5) | 5.2 (4) |
| C(57) | 0.8730 (10) | 0.2084 (8) | −0.2752 (6) | 8.8 (6) |
| C(61) | 0.735 (1) | 0.019 (1) | −0.047 (1) | 16 (1) |
| C(62) | 0.729 (2) | 0.001 (2) | −0.078 (2) | 24 (1) |
| C(71) | 0.536 (2) | 0.0000 | 0.0000 | 26 (1) |
| C(81) | 0.662 (2) | 9.120 (2) | 0.814 (2) | 26 (1) |
| C(82) | 0.691 (2) | 0.087 (2) | 0.753 (2) | 24 (1) |
| C(83) | 0.753 (2) | 0.020 (2) | 0.658 (2) | 23 (1) |
| C(84) | 0.733 (2) | 0.009 (3) | 0.597 (2) | 44 (2) |
| H(1) | 1.1204 | 0.0905 | 0.1013 | 5.5878 |
| H(2) | 1.2087 | 0.1398 | 0.0820 | 6.7367 |
| H(3) | 1.2613 | 0.2344 | 0.0567 | 10.0040 |
| H(4) | 1.2525 | 0.3255 | 0.0209 | 10.7519 |
| H(5) | 1.1530 | 0.3707 | 0.0074 | 10.8575 |
| H(6) | 1.0639 | 0.3210 | 0.0314 | 8.0922 |
| H(7) | 0.8748 | 0.2391 | −0.0279 | 5.4245 |
| H(8) | 0.8422 | 0.3173 | 0.0215 | 6.6911 |
| H(9) | 0.8504 | 0.3783 | 0.0960 | 11.4490 |
| H(10) | 0.9031 | 0.4135 | 0.1646 | 12.4200 |
| H(11) | 1.0044 | 0.3714 | 0.1849 | 11.0598 |
| H(12) | 1.0438 | 0.2943 | 0.1373 | 7.8860 |
| H(13) | 1.0427 | 0.1140 | 0.1964 | 6.2110 |
| H(14) | 1.0889 | 0.0514 | 0.2575 | 6.3302 |
| H(15) | 1.0720 | −0.0810 | 0.1638 | 7.0582 |
| H(16) | 1.0218 | −0.0237 | 0.1007 | 5.7020 |
| H(17) | 0.9953 | 0.2009 | 0.1659 | 5.4997 |
| H(18) | 0.9317 | 0.2426 | 0.2296 | 8.9345 |
| H(19) | 0.8011 | 0.1268 | 0.1914 | 8.1463 |
| H(20) | 0.8659 | 0.0826 | 0.1294 | 6.1492 |
| H(21) | 1.0444 | 0.2546 | −0.0626 | 5.5716 |
| H(22) | 1.1453 | 0.2744 | −0.0916 | 6.0719 |
| H(23) | 1.1914 | 0.1069 | −0.0624 | 6.7403 |
| H(24) | 1.0921 | 0.0874 | −0.0342 | 4.4220 |
| H(25) | 0.8472 | 0.1496 | −0.0621 | 4.3879 |
| H(26) | 0.7962 | 0.1716 | −0.1364 | 5.4485 |
| H(27) | 0.9546 | 0.1950 | −0.2107 | 7.1867 |
| H(28) | 1.0108 | 0.1764 | −0.1344 | 6.4268 |

EXAMPLE 2

Synthesis of [{RuCl((R)-BINAP)}$_2$(μ-Cl)$_3$]$^-$ [Et$_2$NH$_2$]$^+$

In a Schlenk tube were charged 0.43 g (0.5 mmol) of [RuCl(benzene)((R)-BINAP)]Cl and 54 mg (0.5 mmol) of diethylamine hydrochloride, and the tube was purged with nitrogen. To the mixture was added 20 ml of degassed THF, followed by stirring under reflux for 16 hours. Concentration of the reaction mixture gave 0.42 g (98%) of {bis[ruthenium-chloro{(R)-2,2'-bis(diphenylphosphino)-1,1'-binaphthyl}]-μ-trichloro}diethylammonium as a brown solid. Purification was not needed.

$^{31}$P-NMR (CDCl$_3$) δ: 52.12 (d, J=38 Hz), 54.76 (d, J=39 Hz)

EXAMPLE 3

Synthesis of [{RuCl((R)-H$_8$-BINAP)}$_2$($\mu$-Cl)$_3$]$^-$ [Et$_2$NH$_2$]$^+$

In a Schlenk tube were charged 0.44 g (0.5 mmol) of [RuCl(benzene)((R)-H$_8$-BINAP)]Cl and 274 mg (2.5 mmol) of diethylamine hydrochloride, and the tube was purged with nitrogen. To the mixture was added 20 ml of degassed THF, followed by stirring under reflux for 16 hours. The reaction mixture was filtered using Celite, and the filtrate was concentrated to give 0.82 g (96%) of {bis[ruthenium-chloro{(R)-2,2'-bis(diphenylphosphino)-5,5',6,6',7,7',8,8'-octahydro-1,1'-binaphthyl}]-$\mu$-trichloro}diethylammonium as a brown solid. Purification was not needed.

$^{31}$P-NMR (CDCl$_3$) δ: 44.69 (d, J=42 Hz), 50.96 (d, J=41 Hz)

EXAMPLES 4 TO 18

[RuX(arene)(L)]X of formula (II) and R$_2$NH.HX of formula (III) were reacted in the same manner as in Example 2 to obtain [{RuX(L)}$_2$($\mu$-X)$_3$]$^-$[R$_2$NH$_2$]$^+$. The compounds (II) and (III) used are shown in Table 1. The $^{31}$P-NMR spectrum of the resulting complex is also shown in Table 1. Purification was not needed in every reaction.

TABLE 1

| Example No. | [RuX(arene)(L)]X | | | R$_2$NH.HX | | $^{31}$P-NMR Spectrum of |
|---|---|---|---|---|---|---|
| | L* | arene | X | R$_2$NH | X | [{RuX(L)}$_2$($\mu$ − X)$_3$]$^-$[R$_2$NH$_2$]$^+$ |
| 4 | DPPE | benzene | Cl | Et$_2$NH | Cl | 72.1(s) |
| 5 | (S,S)-CHIRAPHOS | benzene | Cl | Et$_2$NH | Cl | 80.78(d,J=37), 87.81(d,J=37) |
| 6 | (2S,4S)-BPPM | benzene | Cl | Et$_2$NH | Cl | 48.76(d,J=41), 53.10(d,J=40) |
| 7 | (S)-(R)-BPPFOM | benzene | Cl | Et$_2$NH | Cl | 46.45(d,J=36), 53.27(d,J=37) |
| 8 | (4R,5R)-DIOP | benzene | Cl | Et$_2$NH | Cl | 36.99(d,J=42), 44.32(d,J=41) |
| 9 | (R)-BIPHEMP | benzene | Cl | Et$_2$NH | Cl | 51.74(d,J=39.9), 52.62(d,J=40) |
| 10 | (R)-DM-BINAP | benzene | Cl | Et$_2$NH | Cl | 54.14(d,J=40.5), 55.58(d,J=40.5) |
| 11 | (S)-Tol-BINAP | p-cymene | Br | Et$_2$NH | Br | 50.35(d,J=35), 54.12(d,J=35) |
| 12 | (R)-DM-BINAP | benzene | Cl | (C$_6$H$_{11}$)$_2$NH | Cl | 50.65(d,J=36), 56.94(d,J=35) |
| 13 | (R)-BINAP | p-cymene | Cl | (iPr)$_2$NH | Cl | 52.00(d,J=38), 52.61(d,J=38) |
| 14 | (R)-BINAP | benzene | Cl | (PhCH$_2$)$_2$NH | Cl | 52.02(d,J=39), 56.22(d,J=38) |
| 15 | (S)-BINAP | benzene | Cl | pyrrolidine | Cl | 51.59(d,J=38), 53.06(d,J=39) |
| 16 | (S)-BINAP | benzene | Cl | L-pyrroline methyl ester | Cl | 51.79(d,J=39), 53.68(d,J=39) |
| 17 | (S)-BINAP | benzene | Cl | (R)-bis(1-phenylethyl)amine | Cl | 51.03(d,J=39), 54.31(d,J=39) |
| 18 | (R)-MeO-BIPHEP | benzene | Cl | Et$_2$NH | Cl | 51.06(d,J=37.6), 54.31(d,J=37.9) |

*The structural formulae of the tertiary phosphine (L) used are shown on the next page.

DPPE: 1,2-Diphenylphosphinoethane (S,S)-CHIRAPHOS:

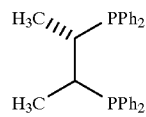

(2S,4S)-BPPM:

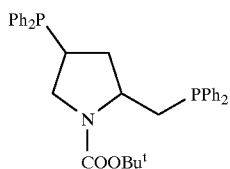

(S)-(R)-BPPFOM:

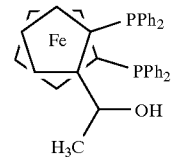

(4R,5R)-DIOP:

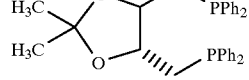

(R)-BIPHEMP:

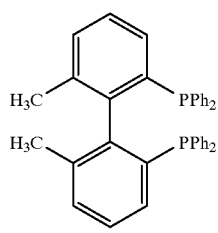

(R)-DM-BINAP:

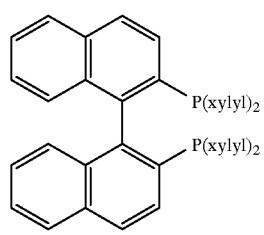

(R)-MeO-BIPHEP:

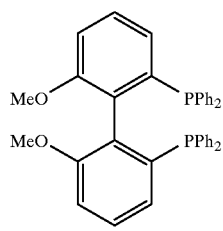

EXAMPLE 19

Synthesis of [{RuCl((S)-BINAP)}$_2$($\mu$-Cl)$_3$]$^-$ [Me$_2$NH$_2$]$^+$

In a Schlenk tube were charged 50 mg (0.2 mmol) of [RuCl$_2$(benzene)]$_2$ (IV), 124 mg (0.2 mmol) of (S)-BINAP (L), and 16 mg (0.2 mmol) of diethylamine hydrochloride (III), and the tube was purged with nitrogen. To the mixture was added 10 ml of degassed THF, followed by stirring under reflux for 16 hours. Concentration of the reaction mixture gave 0.16 g (95%) of {bis[ruthenium-chloro{(S)-2,2'-bis(diphenylphosphino)-1,1'-binaphthyly}]-$\mu$-trichloro}dimethylammonium as a brown solid. Purification was not needed.

$^{31}$P-NMR (CDCl$_3$) $\delta$: 51.82 (d, J=38 Hz), 53.13 (d, J=38 Hz)

EXAMPLES 20 TO 21

The complexes of the present invention were prepared in the same manner as in Example 19, except for using (R)-BINAP as a tertiary phosphine (L) and using dimnethylamine or piperidine as an R$_2$NH moiety of formula (III) as shown in Table 2 below. The $^{31}$P-NMR spectrum of the resulting complex is also shown in the Table. No purification was needed in each reaction.

TABLE 2

| Example No. | [Ru(arene)X$_2$]$_2$ | | L | R$_2$NH.HX | | $^{31}$P-NMR Spectrum of [{RuX(L)}$_2$($\mu$-X)$_3$]$^-$[R$_2$NH]$^+$ |
|---|---|---|---|---|---|---|
| | arene | X | | R$_2$NH | X | |
| 20 | benzene | Cl | (R)-BINAP | Me$_2$MH | Cl | 51.82(d,J=38), 53.13(d,J=38) |
| 21 | benzene | Cl | (R)-BINAP | piperidine | Cl | 51.74(d,J=38), 53.62(d,J=39) |

Comparative Example 1
Preparation of [{RuCl((R)-Tol-BINAP)}$_2$($\mu$-Cl)$_3$]$^-$ [Et$_2$NH$_2$]$^+$ (R)-Tol-BINAP (183 mg, 0.27 mmol), 76 mg (0.27 mmol) of [RuCl$_2$(cod)]$_n$ (wherein cod stands for cyclooctadiene) (available from N. E. Chemcat Ltd.), 30 ml of toluene, and 1 ml of triethylamine were heated at 110° C. for 8 hours while stirring. The reaction mixture was concentrated, and the residue was recrystallized from a mixture of 3 ml of methylene chloride and 20 ml of diethyl ether to give 83 mg (34%) of the title compound as deep red crystals.

Application Example 1

Asymmetric Hydrogenation of Tiglic Acid

Tiglic acid (2-methyl-2-butenoic acid) (6.0 g, 60 mmol) and 2.4 mg (1.4 μmol) of the complex obtained in Example 3, i.e., [{RuCl(R)-H$_8$-BINAP)}$_2$(μ-Cl)$_3$]$^-$[Et$_2$NH$_2$]$^+$, were stirred in a mixture of 2.4 ml of methanol and 9.6 ml of water at 40° C. under a hydrogen pressure of 4 atm for 16 hours. After confirming the completion of the reaction by gas chromatography, the solvent was evaporated to give 5.8 g (96%) of 2-methylbutanoic acid.

Boiling point: 78° C. (15 mmHg)

[α]$_D^{25}$=−17.93° C. (neat)

From the specific rotation, the product was identified to be an (R)-(−)-compound having an optical purity of 94.4% e.e.

Application Example 2

Asymmetric Hydrogenation of 2-Oxopropanol

In a 100 ml stainless steel autoclave were charged 1.4 mg (6.8 μmol) of the [{RuCL((R)-BINAP)}$_2$(μ-Cl)$_3$]$^-$[Et$_2$NH$_2$]$^+$ obtained in Example 2, 2.0 g (27 mmol) of 2-oxopropanol, and 6 ml of methanol, and the mixture was stirred at 54° C. under a hydrogen pressure of 30 atm for 17 hours. As a result of gas chromatographic analysis on the reaction mixture, it was found that the conversion was 100% and the optical purity was 92.8%.

While the invention has been described in detail and with reference to specific examples thereof, it will be apparent to one skilled in the art that various changes and modifications can be made therein without departing from the spirit and scope thereof.

What is claimed is:

1. A ruthenium-diphosphine complex represented by formula (I):

$$[\{RuX(L)\}_2(\mu\text{-}X)_3]^-[R_2NH_2]^+ \quad (I)$$

wherein R represents a hydrogen atom, an alkyl group having 1 to 5 carbon atoms, a cycloalkyl group, a substituted or unsubstituted phenyl group or a substituted or unsubstituted benzyl group; X represents a halogen atom; and L represents a tertiary phosphine, with the proviso that MeO-BINAP is not included within L.

2. A ruthenium-phosphine complex according to claim 1, wherein R is an ethyl group, X is a chlorine atom, L is 2,2'-bis(di-3,5-dixylylphosphino)-1,1'-binaphthyl, 2,2'-bis(diphenylphosphino)-5,5',6,6',7,7',8,8'-octahydro-1,1'-binaphthyl, 2,2'-bis (diphenylphosphino)-6,6'-dimethyl-1,1'-biphenyl, 2,2'-bis(di-p-tolylphosphino)-6,6'-dimethyl-1,1'-biphenyl, 2,2'-bis(diphenylphosphino)-6,6'-dimethyoxy-1,1'-biphenyl or 2,2'-bis (di-p-tolylphosphino)-6,6'-dimethoxy-1,1'-biphenyl.

3. A catalyst for asymmetric hydrogenation which comprises a ruthenium-phosphine complex represented by formula (I):

$$[\{RuX(L)\}_2(\mu\text{-}X_3)]^-[R_2NH_2]^+ \quad (I)$$

wherein R represents a hydrogen atom, an alkyl group having 1 to 5 carbon atoms, a cycloalkyl group, a substituted or unsubstituted phenyl group or a substituted or unsubstituted benzyl group; X represents a halogen atom; and L represents a tertiary phosphine.

4. A process for preparing a ruthenium-phosphine complex represented by formula (I):

$$[\{RuX(L)\}_2(\mu\text{-}X)_3]^-[R_2NH_2]^+ \quad (I)$$

wherein R represents a hydrogen atom, an alkyl group having 1 to 5 carbon atoms, a cycloalkyl group, a substituted or unsubstituted phenyl group or a substituted or unsubstituted benzyl group; X represents a halogen atom; and L represents a tertiary phosphine, comprising reacting a ruthenium complex represented by formula (II):

$$[RuX(arene)(L)]X \quad (II)$$

wherein X and L are as defined above; and arene represents a substituted or unsubstituted phenyl group, and an ammonium salt represented by formula (III):

$$R_2NH \cdot HX \quad (III)$$

wherein R and X are as defined above.

5. A process for preparing a ruthenium-phosphine complex represented by formula (I):

$$[\{RUX(L)\}_2(\mu\text{-}X)_3]^-[R_2NH_2]^+ \quad (I)$$

wherein R represents a hydrogen atom, an alkyl group having 1 to 5 carbon atoms, a cycloalkyl group, a substituted or unsubstituted phenyl group or a substituted or unsubstituted benzyl group; X represents a halogen atom; and L represents a tertiary phosphine, comprising reacting a ruthenium complex represented by formula (IV):

$$[RuX_2(arene)]_2 \quad (IV)$$

wherein X is as defined above, a tertiary phosphine represented by L, and an ammonium salt represented by formula (III):

$$R_2NH \cdot HX \quad (III)$$

wherein R and X are as defined above.

* * * * *